United States Patent [19]
Puterka et al.

[11] Patent Number: 6,027,740
[45] Date of Patent: *Feb. 22, 2000

[54] METHOD FOR PROTECTING SURFACES FROM ARTHROPOD INFESTATION

[75] Inventors: Gary J. Puterka, Shepherdstown, W. Va.; Dennis G. Sekutowski, Stockton, N.J.; David Michael Glenn, Shepherdstown, W. Va.

[73] Assignee: Engelhard Corporation, Iselin, N.J.

[*] Notice: This patent is subject to a terminal disclaimer.

[21] Appl. No.: 08/972,653

[22] Filed: Nov. 18, 1997

Related U.S. Application Data

[63] Continuation-in-part of application No. 08/812,301, Mar. 5, 1997, Pat. No. 5,908,708.

[51] Int. Cl.[7] ............................. A01N 25/04; A01N 25/32
[52] U.S. Cl. ..................... 424/405; 47/58.1; 47/DIG. 11; 71/DIG. 1; 424/406; 424/421; 424/DIG. 10; 427/384; 514/919; 516/79; 516/88
[58] Field of Search ............................. 252/313.1, 313.2, 252/315.2; 427/384; 71/DIG. 1; 424/405, 421, DIG. 10, 684, 687, 406; 516/79, 88, 104; 47/58.1, DIG. 11

[56] References Cited

U.S. PATENT DOCUMENTS

| | | | |
|---|---|---|---|
| 2,441,423 | 5/1948 | Elliot et al. | 252/313.2 X |
| 2,818,340 | 12/1957 | Goddin et al. | 99/2 |
| 2,948,632 | 8/1960 | Albert et al. | . |
| 3,120,445 | 2/1964 | Aluisi et al. | 106/286 |
| 3,124,505 | 3/1964 | Doyle et al. | . |
| 3,159,536 | 12/1964 | Marotta | 424/600 |
| 3,227,657 | 1/1966 | Haden, Jr. et al. | 252/315.2 |
| 3,235,451 | 2/1966 | Odeneal | 424/421 |
| 3,346,507 | 10/1967 | Taulli | 252/315.2 |
| 3,964,649 | 6/1976 | Alexander | 222/399 |
| 4,071,374 | 1/1978 | Minton | 252/315.2 X |
| 4,203,864 | 5/1980 | Sawyer, Jr. | 252/314 |
| 4,274,883 | 6/1981 | Lumbeck et al. | 106/308 |
| 4,279,895 | 7/1981 | Carle | 424/127 |
| 4,382,868 | 5/1983 | House | 252/315.2 X |
| 4,632,936 | 12/1986 | Boase et al. | 514/465 |
| 4,634,463 | 1/1987 | Ohsuga | 71/34 |
| 4,705,816 | 11/1987 | Pole | 523/524 |
| 5,122,518 | 6/1992 | Vrba | 514/63 |
| 5,151,122 | 9/1992 | Atsumi et al. | 424/421 X |
| 5,186,935 | 2/1993 | Tucker | 424/410 |
| 5,392,559 | 2/1995 | Long | 43/52 |
| 5,393,461 | 2/1995 | Fillipova | 252/314 |
| 5,414,954 | 5/1995 | Long | 43/121 |
| 5,455,220 | 10/1995 | Dedolph | 71/DIG. 1 |
| 5,480,638 | 1/1996 | Erwin | 424/614 |

FOREIGN PATENT DOCUMENTS

| | | | |
|---|---|---|---|
| 29 26 095 | 3/1980 | Germany | . |
| 1792257 A3 | 6/1990 | U.S.S.R. | . |
| 225996 | 12/1924 | United Kingdom | 424/687 |
| WO 94 09626 | 5/1994 | WIPO | . |

OTHER PUBLICATIONS

Driggers, B. F. "Experiments with Talc and Other Dusts Used Against Recently Hatched Larvae of the Oriental and Codling Moths, "J. Econ. Ent., 22 327–334 (1929).

Hunt, C.R., "Toxicity of Insecticide Dust Diluents and Carriers to Larvae of the Mexican Bean Beetle," J. Econ. Ent., 40 215–219 (1947).

P. Alexanderm J.A. Kitchener and H.V.A. Briscoe, "Inert Dust Insecticides, " Parts I, II, and III, Ann. Appl. Biol., 31 143–159 (1944).

W. Ebeling, R. F. Wagner "Rapid Desiccation of Drywood Termites with Inert Sorptive Dusts and Other Substances," J Econ. Ent., 52 190–207 (1959).

M. Bar–Joseph, H. Frenkel "Spraying Citrus Plants with Kaolin Suspensions Reduces Colonization by the Spiraea Aphid." Corp Prot 2 371–374 (1983).

J.S. Dhaliwal, "Effect of Rainfall and Kaolinite Spray on the Corn Aphid, Rhopalosiphum Maidis (Fitch) Infesting Barley (Hordeum Vulgare Linn)," Forage Res. 5:155–157 (1979).

A. Boyce, "Mortality of Rhagoletis Completa Cress. (Diptera:Trypetidae) Through Ingestion of Certain Solid Materials," J. Econ Ent 25 1053–1059 (1932).

*Primary Examiner*—Richard D. Lovering
*Attorney, Agent, or Firm*—Raymond F. Keller

[57] ABSTRACT

Disclosed is a method for protecting surfaces from arthropod infestation which involves treating the surface with an effective amount of finely divided calcined kaolins, hydrophobic calcined kaolins, hydrous kaolins, hydrophobic hydrous kaolins, hydrophobic calcium carbonates, calcium carbonates or mixtures thereof.

15 Claims, No Drawings

METHOD FOR PROTECTING SURFACES FROM ARTHROPOD INFESTATION

CROSS-REFERENCE TO RELATED APPLICATIONS

This application is a continuation-in-part of U.S. patent application Ser. No. 08/812,301, filed Mar. 5, 1997 and now U.S. Pat. No. 5,908,708, which is incorporated herein by reference for its teachings related to the invention disclosed herein.

FIELD OF THE INVENTION

The present invention is directed to a method for protecting surfaces from arthropod infestation by using certain nontoxic particulate materials.

BACKGROUND OF THE INVENTION

The prior art has discussed the use of certain inert particulate solids as insecticides, see for example; Driggers, B. F., "Experiments with Talc and Other Dusts Used Against Recently Hatched Larvae of the Oriental and Codling Moths," *J. Econ. Ent.*, 22 327–334 (1929); Hunt, C. R., "Toxicity of Insecticide Dust Diluents and Carriers to Larvae of the Mexican Bean Beetle," *J. Econ. Ent.*, 40 215–219 (1947); P. Alexander, J. A. Kitchener and H. V. A. Briscoe, "Inert Dust Insecticides," Parts I, II, and III, *Ann. Appl. Biol.*, 31 143–159, (1944), which concluded that ". . . the relative killing powers of different dusts run parallel with their capacities for promoting evaporation."; Chiu, S. F., "Toxicity Studies of So-Called 'Inert' Materials with the Rice Weevil and the Granary Weevil," *J. Econ. Entomol.* 32 810–821 (1939); David, W. A. L. and B. O. C. Gardiner "Factors Influencing the Action of Dust Insecticides," *Bull. Entomol. Res.*, 41 1–61(1950); Ebling, W. and R. E. Wagner, "Rapid Desiccation of Drywood Termites with Inert Sorptive Dusts and Other Substances," *J. Econ. Entomol.* 52 190–207 (1959); Bar-Joseph, M. and H. Frenkel, "Spraying Citrus Plants with Kaolin Suspensions Reduces Colonization by the Spirea Aphid," *Crop Prot.* 2 371–374 (1983); Farmer, A. M., "The Effect of Dust on Vegetation—a Review," *Environ. Pollut.* 79: 63–75 (1993); Dahliwal, J. S., "Effect of Rain Fall and Kaolinite Spray on the Corn Leaf Aphid Infesting Barley," *Forage Res.* 5 155 (1979) and U.S. Pat. Nos. 3,159,536 (1964), 3,235,451 (1965), 5,122,518 (1992) and 5,414,954 (1995). In particular '954 relates to "methods and means of selectively controlling the movement of crawling arthropods and more particularly to nontoxic non-debilitating methods and means for causing crawling arthropods to abandon sites they have infested or for discouraging crawling arthropods from infesting a site where they are not wanted." According to '954 this is accomplished by "a method of restricting crawling arthropods from climbing onto a skewed surface comprising forming an adherent, continuous, substantially uniformly thick coating on said surface by applying thereto a dispersion of minus 10 micron titanium dioxide particles in a liquid and '954" specifically refers to a "method wherein said crawling arthropods are cockroaches," each of which is incorporated herein by reference with regard to its teachings relating to particulate materials.

Chemical insecticides have been used extensively in horticultural crop production to control certain arthropod pests such as arthropods and mites. These chemical insecticides generally belong to the following types of chemical compounds: inorganic (sodium fluoaluminate), organic (dithiocabamates, organophosphates), and antibiotic (agrimectins, spinosins). These chemical insecticides are physiological toxins that kill arthropod pests. Additional insecticidal classes are hormonal (phenoxyphenoxy) that kill arthropods by physiologically disrupting the growth processes, biologicals (entomopathogenic fungi, bacteria, and viruses) that kill by causing fatal diseases, soaps (potassium salts of fatty acids) that kill by suffocation, and diatomaceous earth that kills by desiccation.

The above references refer to particulate solids that are toxic to arthropods and kill these pests.

There is still a need for an effective nontoxic method for protecting surfaces from arthropod infestation based on particulate materials that are not considered harmful to mammals, birds, fish, beneficial arthropods, and the environment.

SUMMARY OF THE INVENTION

A method for protecting surfaces from arthropod infestation which comprises applying to said surface an effective amount of one or more particulate materials selected from the group consisting of calcined kaolins, hydrophobic calcined kaolins, hydrous kaolins, hydrophobic hydrous kaolins, hydrophobic calcium carbonates, calcium carbonates and mixtures thereof, said particulate materials being finely divided.

DETAILED DESCRIPTION OF THE INVENTION

This invention relates to a method for protecting surfaces from arthropod infestation. The arthropods controlled by this invention (as well as the damage resulting therefrom) refer to arthropods including insects, mites, spiders and related animals. This invention is particularly effective in controlling damage caused by crawling, hopping or flying arthropod pests without using insecticides or physiological toxins that are harmful to human health and the environment. In addition, the method of this invention is non-toxic to many beneficial arthropods such as lady beetles and honey bees. Inclusive are other types of damage to crops commonly caused by arthropod transmission of disease such as the fungus disease, Dutch Elm disease, of American Elm by the European elm beetle; the bacterial disease, Fire blight, of apples and pears by flies, beetles and other insects; the virus disease, Curly Top, of sugar beats by the beet leaf hopper. Damage control also applies to those secondary infections of wound sites on a plant that result from arthropod feeding such as brown rot infection of stone fruits that results when the disease organism enters the plant through plum curculio feeding sites.

The instant invention provides a nontoxic environment that is effective at protecting surfaces against a broad-spectrum of arthropod pest activity by being effective against arthropods that crawl, hop and fly. Although some arthropods may die as a result of contacting the particles of this invention, the primary function of the treatment of this invention is to affect arthropod behavior instead of killing the arthropod and, therefore is not considered harmful to many beneficial insects such as ladybugs and honeybees. While not being bound by theory, the effects of the particle treatment of this invention protect the surface by creating a hostile environment on the surface that repels arthropod pests such that they will not feed, lay eggs, or colonize and, therefore, will not infest or will abandon the treated site by making the surface become unrecognizable by feel, sight or otherwise and/or unpalatable or otherwise unsuitable as a food source or for colonization by arthropod pests failure to recognize the particle-altered surface or otherwise. These effects will vary by arthropod species and size. The particulate treatment does not need to have a smooth surface or one that is set at least a 20 degree angle to the horizon or a continuous coating free of bubbles and voids. A complete coating of the surface is desirable although certain gaps and voids are expected but will not influence the overall arthropod controlling feature of the treatment. The particles useful for this invention can be applied to surfaces that are horizontal or inclined, smooth or rough, or complex or simple in structure and a continuous bubble and void free film is not required for the particle treatment to be effective against most arthropods.

The surfaces to which this invention relate include surfaces that are subject to arthropod infestation and include, for example, man-made structures made of wood, concrete, plastic pipe, electrical cable etc. and include household applications such as protecting plumbing, clothes closets, food cabinets, electrical wiring, foundation, framing, basements, etc.; livestock; soils including rangeland; stored agricultural products such as grains, seeds etc.; and agricultural and ornamental crops and the products thereof, including those selected from the group consisting of fruits, vegetables, trees, flowers, grasses, roots, and landscape and ornamental plants.

The particulate materials useful for the purposes of this invention are selected from the group consisting of calcined kaolins, hydrophobic calcined kaolins, hydrous kaolins, hydrophobic hydrous kaolins, hydrophobic calcium carbonates, calcium carbonates and mixtures thereof.

Calcined kaolin is will known to those of ordinary skill in the art and can be prepared by calcining hydrous kaolin which is generally represented by the formula $Al_4Si_4O_{10}(OH)_8$. The calcined kaolin of this invention will usually have been subject to calcination temperature conditions in excess of about 350° C., more typically in excess of about 500° C. and preferably between about 500° C. and about 1100° C.

Calcium carbonate is a commonly available material. It occurs in nature as, for example, aragonite, calcite, chalk, dolomite, limestone, etc. or may be prepared synthetically by precipitation from the reaction of calcium chloride and sodium carbonate in water or by passing carbon dioxide through a suspension of hydrated lime in water.

Calcined kaolins, hydrous kaolins, and calcium carbonates are normally hydrophilic but their surfaces can be made hydrophobic by addition of hydrophobic wetting agents. Many industrial mineral applications, especially in organic systems such as plastic composites, films, organic coatings or rubbers, are dependent upon just such surface treatments to render the mineral surface hydrophobic; see, for example, Jesse Edenbaum, *Plastics Additives and Modifiers Handbook*, Van Nostrand Reinhold, New York, 1992, pages 497–500 which is incorporated herein by reference for teachings of such surface treatment materials and their application. So-called coupling agents such as fatty acids and silanes are commonly used to surface treat solid particles as fillers or additives targeted to these industries. Such hydrophobic agents are well known in the art and common examples include: organic titanates such as Tilcom® obtained from Tioxide Chemicals; organic zirconate or aluminate coupling agents obtained from Kenrich Petrochemical, Inc.; organofunctional silanes such as Silquest® products obtained from Witco or Prosil® products obtained from PCR; modified silicone fluids such as the DM-Fluids obtained from Shin Etsu; and fatty acids such as Hystrene® or Industrene® products obtained from Witco Corporation or Emersol® products obtained from Henkel Corporation (stearic acid and stearate salts are particularly effective fatty acids and salts thereof for rendering a particle surface hydrophobic).

The term "hydrophobic" as used herein with respect to particulate materials of calcined kaolins, hydrous kaolins, and calcium carbonates shall mean that the surface of such particles are made hydrophobic by addition of hydrophobic wetting agents as described hereinabove.

Examples of preferred particulate materials suitable for the purposes of this invention that are commercially available from Engelhard Corporation, Iselin, N.J. are the hydrous kaolins sold under the trademark ASP®, calcined kaolins sold under the trademark Satintone® and the siloxane treated calcined kaolins sold under the trademark Translink®; and calcium carbonate commercially available from English China Clay under the trademarks Atomite® and Supermite® and stearic acid treated ground calcium carbonates commercially available from English China Clay under the trademarks Supercoat® and Kotamite®.

The term "finely divided" when utilized herein means that the particulate materials have a median individual particle size below about 10 microns and preferably below about 3 microns and more preferably the median particle size is about one micron or less. Particle size and particle size distribution as used herein are measured with a Micromeritics Sedigraph 5100 Particle Size Analyzer. Measurements were recorded in deionized water for hydrophilic particles. Dispersions were prepared by weighing 4 grams of dry sample into a plastic beaker adding dispersant and diluting to the 80 ml mark with deionized water. The slurries were then stirred and set in an ultrasonic bath for 290 seconds. Typically, for kaolin 0.5% tetrasodium pyrophosphate is used as a dispersant; with calcium carbonate 1.0% Calgon T is used. Typical densities for the various powders are programmed into the sedigraph, e.g., 2.58 g/ml for kaolin. The sample cells are filled with the sample slurries and the X-rays are recorded and converted to particle size distribution curves by the Stokes equation. The median particle size is determined at the 50% level.

Preferably, the particulate material has a particle size distribution wherein up to 90% by weight of the particles have a particle size of under about 10 microns, preferably below about 5 microns and more preferably about one micron or less.

The particulate materials particularly suitable for use in this invention are nontoxic.

The particulate materials are preferably nontoxic meaning that they are not physiological toxins and, in the limited quantities needed affect arthropod behavior to reduce arthropod infestation, such materials are not considered harmful to mammals, birds, and fish as well as well as arthropods, the environment, the applicator and the ultimate consumer.

This treatment when applied to horticultural crops should not materially affect the exchange of gases on the surface of said crop. The gases which pass through the particle treatment are those which are typically exchanged through the surface skin of living plants. Such gases typically include water vapor, carbon dioxide, oxygen, nitrogen and volatile organics.

The surface to be protected is treated with an amount of one or more particulate materials selected from the group consisting of calcined kaolins, hydrophobic calcined kaolins, hydrous kaolins, hydrophobic hydrous kaolins, hydrophobic calcium carbonates, calcium carbonates and mixtures thereof, that is effective in protecting the surface from arthropod infestation. The treatment coverage of said surface is within the skill of the ordinary artesian. Less than full surface coverage is within the scope of this invention and can be highly effective, for example, with respect to horticultural crops neither the under surface of the crop (that which is not exposed directly to the source of light) need be treated by the method of this invention nor must the upper surface of the crop be completely covered; although full crop coverage can provide additional benefits such as effective disease control, smoother fruit surface, reduced bark and fruit cracking, and reduced russetting. Reference is made to U.S. Ser. No. 08/972,648, filed concurrently herewith on Nov. 18, 1997, entitled "Treated Horticultural Substrates" which is incorporated herein by reference for its teachings regarding methods for achieving these additional benefits. The method of this invention may result in the residue of the treatment forming a membrane of one or more layers of said particulate materials on the surface to be treated.

The particulate materials useful for the purposes of this invention may be applied as a dust or as a slurry of finely divided particles in a volatile liquid such as water, a low boiling organic solvent or low boiling organic solvent/water mixture. Adjuvants such as surfactants, dispersants or spreaders/stickers (adhesives) may be incorporated in preparing an aqueous slurry of the particulate materials of this invention. One or more layers of this slurry can be sprayed or otherwise applied to the surface. The volatile liquid is preferably allowed to evaporate between coatings. The residue of this treatment may be hydrophilic or hydrophobic. Applying particles as a dust may be achieved by sprinkling, pouring, or dusting said particles directly on the surface to be protected as an alternative method for carrying out the method of this invention.

Surfactants that are anionic, cationic or nonionic materials; and/or spreader/stickers that can be mixed with the particles useful for this invention (3% or more solids in water) to aid in spraying uniform treatments on the surfaces to be treated are: modified phthalic glycerol alkyd resins such as Latron B-1956 from Rohm & Haas Co.; Plant oils such as cotton seed oil, or plant oil based materials (cocodithalymide) with emulsifiers such as Sea-wet from Salsbury lab, Inc. or; Polymeric terpenes such as Pinene II from Drexel Chem. Co.; nonionic detergents (ethoxylated tall oil fatty acids) such as Toximul 859 and Ninex MT-600 series from Stephan.

The particle treatment may be applied as one or more layers of finely divided particulate material. The amount of material applied is within the skill of one of ordinary skill in the art. The amount will be sufficient to repel or otherwise affect arthropod behavior and/or colonization on the surface to which these particles are applied. For example, this can typically be accomplished by applying from about 25 up to about 5000 micrograms of particulate material/cm$^2$ of surface for particles having specific density of around 2–3 g/cm$^3$, more typically from about 100 up to about 3000 and preferably from about 100 up to about 500. In addition, environmental conditions such as wind and rain may reduce coverage of the particulate materials on the protected surface and, therefore, it is within the scope of this invention to apply the said particles to the surface being protected one or more times so as to maintain the desired effect of invention.

The low boiling organic liquids useful in the present invention are preferably water-miscible and contain from 1 to 6 carbon atoms. The term "low boiling" as used herein shall mean organic liquids which have a boiling point generally no more than 100° C. These liquids enable the particulate solids to remain in finely divided form without significant agglomeration. Such low boiling organic liquids are exemplified by: alcohols such as methanol, ethanol, propanol, i-propanol, i-butanol, and the like, ketones such as acetone, methyl ethyl ketone and the like, and cyclic ethers such as ethylene oxide, propylene oxide and tetrahydrofuran. Combinations of the above-mentioned liquids can also be employed. Methanol is the preferred low boiling organic liquid.

Low boiling organic liquids may be employed in applying the particles to surfaces for the purposes of this invention. Typically, the liquids are used in an amount sufficient to form a dispersion of the particulate material. The amount of liquid is typically up to about 30 volume percent of the dispersion, preferably from about 3 up to about 5 volume percent, and most preferably from about 3.5 to about 4.5 volume percent. The particulate material is preferably added to a low boiling organic liquid to form a slurry and then this slurry is diluted with water to form an aqueous dispersion. The resulting slurry retains the particles in finely divided form wherein most of the particles are dispersed to a particle size of less than about 10 microns.

The following examples are illustrative of embodiments of the invention and are not intended to limit the invention as encompassed by the claims forming part of the application.

EXAMPLE I

Acute toxicity of a hydrophilic kaolin made hydrophobic by treatment with siloxane, Translink® 77, on adult honey bees. Percent mortality was determined 48 hours after exposure to different concentrations of kaolin solubilized in 2 $\mu$l of methanol. Mortalities were compared to an untreated control and solvent control. Applications were made topically to 20 adult bees per treatment with 3 replications per treatment. Data is a summary of an acute honey bee toxicity test conducted by Wildlife International, LTD. (Proj. No. 469-101) for Engelhard Corporation.

TABLE I

| Honey bee mortality 48 hours after Translink ® 77 | | |
| --- | --- | --- |
| Treatment | Dose ($\mu$g a.i./bee) | % Mortality |
| Untreated | none | 0.3 |
| Solvent control | 2 $\mu$l methanol | 0.0 |
| Translink 77 | 6.25 | 0.0 |
| | 12.5 | 0.0 |
| | 25.0 | 0.3 |
| | 100.0 | 0.0 |

Translink ® 77 siloxane treated kaolin (Engelhard Corporation).

This study shows that Translink® 77 is nontoxic to honey bees at a broad range of concentrations.

EXAMPLE II

Acute toxicity of a hydrophilic kaolin made hydrophobic by siloxane treatment, Translink® 77, on lady beetle adults as compared to untreated control and toxic conventional insecticide.

Applications were applied 25 pounds material suspended in 4 gal methanol and added to 100 gal water. These treatments were applied at the total output of 125 gal/acre using an orchard handgun sprayer. There were 5 replications per treatment with single tree replicates. Lady beetle mortality was determined by counting the number of dead lady beetles on the ground in a 3 foot diameter around the base of each treated tree. Detrimental effect of applications on live lady beetle numbers within treated trees was determined by counting total number within each treated tree. Data was analyzed using ANOVA and means were compared using the least significant differences method, LSD, at P=0.05.

TABLE II

Mean (±SE) number of live lady beetle adults within the tree and dead lady beetles on the ground around each treated tree in a pear orchard 2 days after treatment, August 8, 1997, Kearneysville, WV.

| Treatment | Concentration | No. Lady beetles/tree | Dead lady beetles on ground/tree |
|---|---|---|---|
| Translink ® 77 Kaolin | 0.3% in $H_2O$ | 3.8 ± 1.1 a | 0.0 ± 0.0 b |
| Agrimek (avermectin) | 5.0 oz. a.i./acre | 1.4 ± 0.7 b | 3.6 ± 0.7 a |
| Untreated control | — | 5.4 ± 0.9 a | 0.0 ± 0.0 b |

Means within a column followed by the same letter are not significantly different (p > 0.05, LSD).

Data indicates that siloxane treated hydrophobic kaolin particle, Translink® 77, was not harmful to lady beetle populations within trees treated with this compound in comparison to the untreated control. Furthermore, lady beetles were not killed by the Translink® 77 treatment although the toxic chemical, Agrimek®, did. This study shows that Translink® 77 is nontoxic to beneficial lady beetles.

EXAMPLE III

This example demonstrates how kaolin and calcium carbonate particle barriers are repellent and/or deterrent to egg laying by pear psylla. Ten adults were given a free choice between pear leaves treated with various types of calcium carbonate and kaolin particles that are hydrous, calcined or made hydrophobic by treatment with siloxane or stearate. Leaves were sprayed with a solution comprised of 5% particles and 10% methanol in water using a hand held sprayer. Treatments included untreated and a 10% MEOH controls. Five mating pairs of adult pear psylla (n=10) were released within a caged arena containing all eleven particle and untreated control treatments. The experiment was a randomized block design with 5 replications. Adult and egg numbers were recorded 24 hours after being released within the arena. Data was subjected to ANOVA and means were separated using LSD, P=0.05.

TABLE III

Repellant and oviposition deterrent effects of pear leaves treated with kaolin and calcium carbonate particle treatments on pear psylla adults.

| Particle type | Treatment | Number present 24 hours after exposure | |
|---|---|---|---|
| | | Adults | Eggs |
| — | Control | 3.60 ± 1.47 AB | 15.8 ± 7.69 A |
| — | Methanol Control | 4.40 ± 0.51 A | 9.40 ± 4.24 AB |
| Kaolin | ASP 900 - hydrous[1] | 5.20 ± 1.24 A | 7.20 ± 5.50 BC |
| | ASP 900 - hydrophobic[2] | 1.00 ± 0.77 CDE | 0.00 ± 0.00 C |
| | Satintone-W - calcined[3] | 2.40 ± 0.60 BC | 0.00 ± 0.00 C |

TABLE III-continued

Repellant and oviposition deterrent effects of pear leaves treated with kaolin and calcium carbonate particle treatments on pear psylla adults.

| Particle type | Treatment | Number present 24 hours after exposure | |
|---|---|---|---|
| | | Adults | Eggs |
| | Satintone-W - hydrophobic[4] | 1.00 ± 0.45 CDE | 0.00 ± 0.00 C |
| | Translink 37 - hydrophobic[5] | 0.00 ± 0.00 E | 0.00 ± 0.00 C |
| | Translink 77 - hydrophobic[5] | 0.40 ± 0.40 DE | 0.00 ± 0.00 C |
| Calcium carbonate | Kotomite - hydrophobic[6] | 0.00 ± 0.00 E | 0.00 ± 0.00 C |
| | Atomite - hydrophillic[7] | 1.80 ± 0.58 BCDE | 0.00 ± 0.00 C |

[1]ASP ® 900 (Engelhard Corporation)
[2]ASP ® 900 (Engelhard Corporation) treated with stearate.
[3]Satintone ® W (Engelhard Corporation)
[4]Satintone ® W (Engelhard Corporation) treated with stearate
[5]Translink ® 37 and 77 (Engelhard Corporation)
[6]Kotamite ® (ECC Int.)
[7]Atomite ® (ECC Int.)
Means within a column followed by the same letter are not significantly different, LSD, P = 0.05; mean of 5 replications.

Results demonstrate that these particles are repellent to adults in that they will not settle upon hydrophobic or calcined kaolin or hydrophobic calcium carbonate particle treated pear leaves. Data indicate that the repellent nature of these particles increases when hydrophilic materials are calcined or when hydrophilic materials are made hydrophobic.

EXAMPLE IV

"Red Delicious" apple trees received the following treatments: 1) no treatment, 2) weekly application of siloxane treated hydrophobic kaolin particle, Translink® 77, beginning in Mar. 11, 1997, 3) weekly applications of calcined hydrophilic kaolin particle, Satintone® 5HB, beginning in Apr. 29, 1997, and 4) weekly application of stearate treated hydrophobic calcium carbonate, SuperCoat®, (commercially available from English China Clay) beginning in Apr. 29, 1997. Kaolin and calcium carbonate treatments were applied 25 pounds material suspended in 4 gal methanol and added to 100 gal water. Satintone® 5HB applied 25 pounds material suspended in 100 gal water with the addition of 27 oz Ninex® MT-603 and 2 pints Toximul®. These treatments were applied at the total output of 125 gal/acre using an orchard sprayer. The treatments were arranged in a randomized complete block design with 4 replications and 3 trees/plot. Treatments were not irrigated and received 21.58 cm of precipitation from May 1 to Aug. 30, 1997. Fruit were harvested at maturity; fruit number were measured at harvest. Data were analyzed using Analysis of Variance (ANOVA) and treatment means were separated using least significant difference method (LSD) at P=0.05.

TABLE IV

Mean ( ± ) arthropod numbers per terminal in various treatments on 'Red Delicious' apples on 7/1/97. There were 4 replications per treatment and 25 terminals per replication, Kearneysville, WV.

| Arthropod | Untreated | Translink 77 Kaolin | Satintone 5HB Kaolin | SuperCoat Calcium Carb. |
|---|---|---|---|---|
| Pests | | | | |
| Mites | 67.5 ± 27.2 a | 1.5 ± 0.9 b | 3.8 ± 1.4 b | 45.8 ± 18.2 a |
| Leafhoppers | 61.0 ± 16.0 a | 8.0 ± 5.2 b | 16.5 ± 2.3 b | 44.8 ± 7.7 a |
| Thrips | 4.5 ± 1.9 a | 0.5 ± 0.5 b | 1.0 ± 0.6 b | 3.0 ± 0.7 ab |
| Leaf Miners | 0.0 ± 0.0 a | 1.0 ± 0.6 a | 0.5 ± 0.3 a | 0.8 ± 0.5 a |
| Beneficials | | | | |
| Lacewing Eggs | 1.8 ± 0.6 ab | 2.3 ± 0.5 ab | 0.8 ± 0.8 b | 0.3 ± 0.3 b |
| Lacewing Larvae | 0.0 ± 0.0 a | 0.3 ± 0.3 a | 0.5 ± 0.3 a | 0.0 ± 0.0 a |
| Lady Beetle Larvae | 0.0 ± 0.0 b | 1.3 ± 1.0 b | 4.8 ± 2.2 a | 0.3 ± 0.3 b |
| Lady Beetle Adult | 0.0 ± 0.0 a | 0.5 ± 0.5 a | 0.8 ± 0.5 a | 0.3 ± 0.3 a |

Means within a column followed by the same letter are not significantly different, LSD, P = 0.05.

After 10 applications of the kaolin treatments gave the same or better levels of control of mites, leafhoppers, and thrips. The calcium carbonate treatment gave the same levels of control as kaolin treatments except for mites and leafhoppers. The kaolin and/or calcium carbonate treatments either did not significantly lower or increased beneficial arthropod numbers as compared to the untreated control block. No plant toxicity was noted in any treatment. Conclusion from this data is that the kaolin and/or calcium carbonate treatments are effective against a broad range of arthropod pests without being harmful to beneficial arthropods.

EXAMPLE V

Arthropod pest control in blackberries after 6 weekly applications of siloxane treated hydrophobic kaolin particle, Translink® 77, as compared to an untreated control. Applications were treatments were applied at 25 pounds material suspended in 4 gal methanol and added to 100 gal water. These treatments were applied at the total output of 125 gal/acre using an orchard sprayer. There were 3 replications per treatment. Arthropod counts were determined as average numbers per terminal from 10 terminals per treatment. Counts were made on Jun. 24, 1997. Data were analyzed using Analysis of variance and treatment means were separated using least significant difference method (LSD) at P=0.05.

TABLE V

Mean (±SE) numbers of arthropods per terminal after 6 weekly applications of Translink ® 77 kaolin on blackberry, June 24, 1997, Kearneysville, WV

| | Untreated | Translink ® 77 Kaolin |
|---|---|---|
| Leafhoppers | 57.8 ± 9.2 a | 0.7 ± 0.3 b |
| Thrips | 3.5 ± 0.9 a | 0.7 ± 0.3 b |
| Aphids | 7.2 ± 2.4 a | 0.7 ± 0.5 b |
| Psylla Damage[1] | 20.7 ± 4.6 a | 0.8 ± 0.5 b |

Means within a column followed by the same letter are not significantly different, LSD, P = 0.05.
[1]Numbers represent whole block counts.

Data demonstrates that siloxane treated hydrophobic kaolin particles, Translink® 77, are very effective control agents against a broad range of arthropod pests of blackberry.

What is claimed is:

1. A method for protecting surfaces from arthropod infestation which comprises applying to said surface an effective amount of a slurry comprising one or more particulate materials selected from the group consisting of calcined kaolins, hydrophobic calcined kaolins, hydrophobic calcium carbonates, calcium carbonates and mixtures thereof, said particulate materials being finely divided, wherein the surface is selected from the group consisting of fruits, vegetables, trees, flowers, grasses, roots and landscape and ornamental plants and said particulate materials as applied allow for the exchange of gases on the surface.

2. The method of claim 1 wherein the particulate material has a particle size distribution wherein up to 90% of the particles have a particle size of under about 10 microns.

3. The method of claim 1 wherein said hydrophobic calcined kaolins, and hydrophobic calcium carbonates have a hydrophobic outer surface prepared from materials selected from the group consisting of organic titanates, organic zirconate or aluminate coupling agents, organofunctional silanes, modified silicone fluids and fatty acids and salts thereof.

4. The method of claim 1 wherein the surface is a horticultural crop selected from the group consisting of agricultural and ornamental crops.

5. The method of claim 4 wherein the horticultural crop is selected from the group consisting of fruits, vegetables, and trees.

6. The method of claim 1 wherein the finely divided particulate materials have a median individual particle size below about 3 microns.

7. The method of claim 1, wherein the slurry further comprises a low boiling organic liquid.

8. A method for protecting horticultural crops from arthropod infestation which comprises applying to the surface of a horticultural crop selected from the group consisting of fruits, vegetables, trees, flowers, grasses, roots and landscape and ornamental plants an effective amount of a slurry comprising water and one or more particulate materials selected from the group consisting of calcium carbonate, calcined kaolin, and mixtures thereof, permitting the slurry to dry, said particulate materials have a median individual particle size of about one micron or less, and wherein said particles as applied allow for the exchange of gases on the surface of said crop.

9. The method of claim 1 or 8 wherein the finely divided particulate materials are applied one or more times during the growing season of said horticultural crop.

10. The method of claim 8, wherein the slurry further comprises a low boiling organic liquid.

11. A method for protecting surfaces from arthropod infestation which comprises applying to the surfaces selected from the group consisting of fruits, vegetables, trees, flowers, grasses, roots and landscape and ornamental plants, an effective amount of a slurry comprising water and one or more particulate materials selected from the group consisting of calcined kaolins, hydrophobic calcined kaolins, hydrophobic calcium carbonates, calcium carbonates and mixtures thereof, said particulate materials being finely divided, wherein said particulate materials as applied allow for the exchange of gases on the surface.

12. The method of claim 11, wherein particulate materials have a particle size distribution wherein up to 90% of the particles have a particle size of under about 10 microns.

13. The method of claim 11, wherein particulate materials have a particle size distribution wherein up to 90% of the particles have a particle size of under about 3 microns.

14. The method of claim 11, wherein particulate materials have a particle size distribution wherein up to 90% of the particles have a particle size of under about 1 micron.

15. The method of claim 11, wherein the slurry further comprises a low boiling organic liquid.

* * * * *

UNITED STATES PATENT AND TRADEMARK OFFICE
CERTIFICATE OF CORRECTION

PATENT NO. : 6,027,740
DATED : February 22, 2000
INVENTOR(S) : Gary J. Puterka, Dennis G. Sekutowski, David Michael Glenn It is certified that error appears in the above-identified patent and that said Letters Patent is hereby corrected as shown below:

Title page,
Item [73], the Assignees should read "Engelhard Corporation, Iselin, New Jersey, USA" and "The United States of America, as represented by the Secretary of Agriculture, Washington, D.C., USA".

Signed and Sealed this

Ninth Day of October, 2001

*Attest:*

NICHOLAS P. GODICI
*Attesting Officer*    *Acting Director of the United States Patent and Trademark Office*